United States Patent
Capanni

(10) Patent No.: US 7,361,177 B2
(45) Date of Patent: Apr. 22, 2008

(54) SYSTEM AND METHOD FOR PROVIDING FASTENING ELEMENTS FOR A BONE PLATE

(75) Inventor: Felix Capanni, Freiburg (DE)

(73) Assignee: Stryker Leibinger GmbH & Co. KG, Freiburg (DE)

( * ) Notice: Subject to any disclaimer, the term of this patent is extended or adjusted under 35 U.S.C. 154(b) by 482 days.

(21) Appl. No.: 10/446,534

(22) Filed: May 28, 2003

(65) Prior Publication Data

US 2004/0049193 A1    Mar. 11, 2004

(30) Foreign Application Priority Data

May 29, 2002    (DE)    ................ 102 24 005

(51) Int. Cl.
*A61B 17/56*    (2006.01)
(52) U.S. Cl. ............... 606/69; 606/71; 606/70; 606/68
(58) Field of Classification Search ................ 606/69, 606/70, 72, 73; 269/289 R, 307, 909, 900; 623/17.17, 6.45, 919
See application file for complete search history.

(56) References Cited

U.S. PATENT DOCUMENTS

| 2,267,008 | A | * | 12/1941 | Zimmer | ................ | 211/69 |
| 4,943,292 | A | * | 7/1990 | Foux | ................ | 606/70 |
| 5,531,747 | A | * | 7/1996 | Ray | ................ | 606/61 |
| 6,235,034 | B1 | * | 5/2001 | Bray | ................ | 606/71 |

FOREIGN PATENT DOCUMENTS

EP    1120090    *    8/2001

* cited by examiner

*Primary Examiner*—Corrine McDermott
*Assistant Examiner*—David Izquierdo
(74) *Attorney, Agent, or Firm*—Howard & Howard Attorneys, P.C.

(57) ABSTRACT

A system for the provision of fastening elements during a surgical intervention and a method of surgically removing a bone segment are described. The system comprises a bone plate having openings arranged in a first pattern for receiving fastening elements, as well as a receiving surface having a plurality of openings for temporarily receiving the fastening elements. The openings of the receiving surface are arranged in a second pattern, which is at least in sections identical or similar to the first pattern.

27 Claims, 3 Drawing Sheets

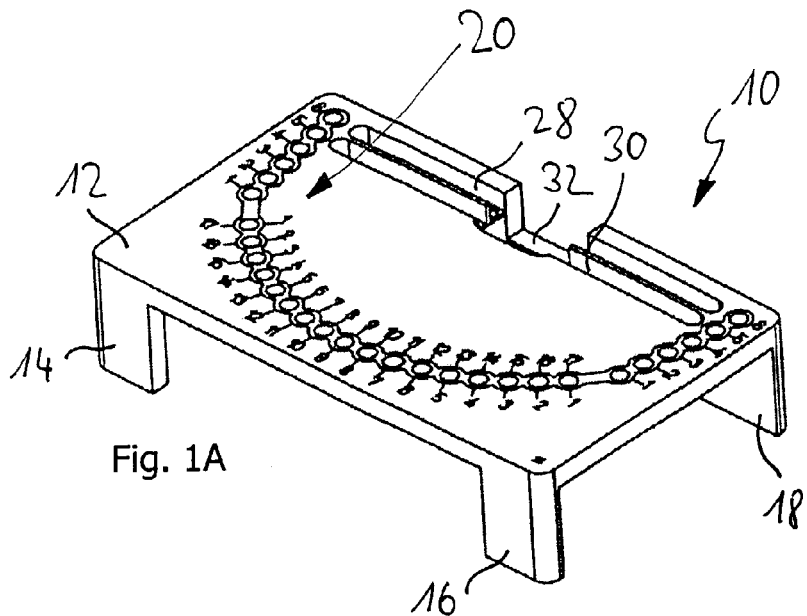
Fig. 1A
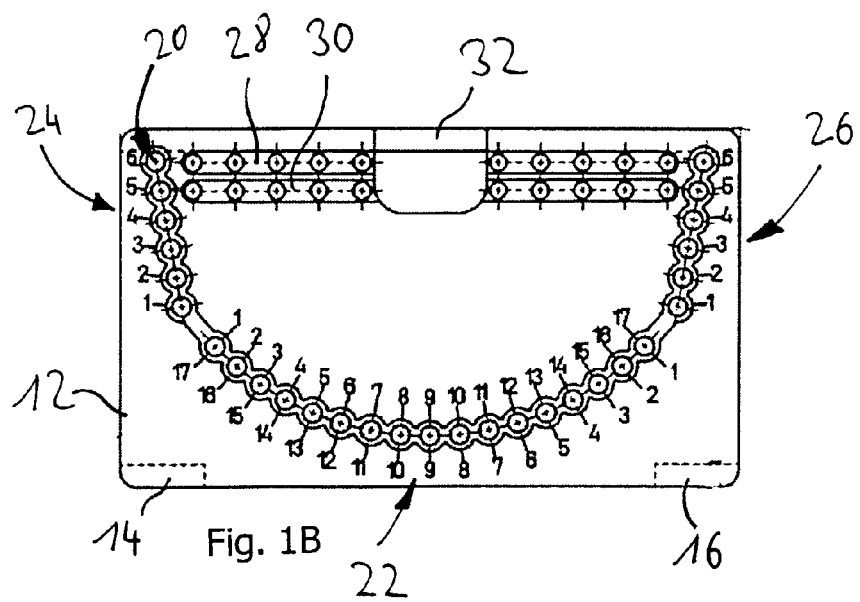
Fig. 1B
Fig. 1C
Fig. 1D

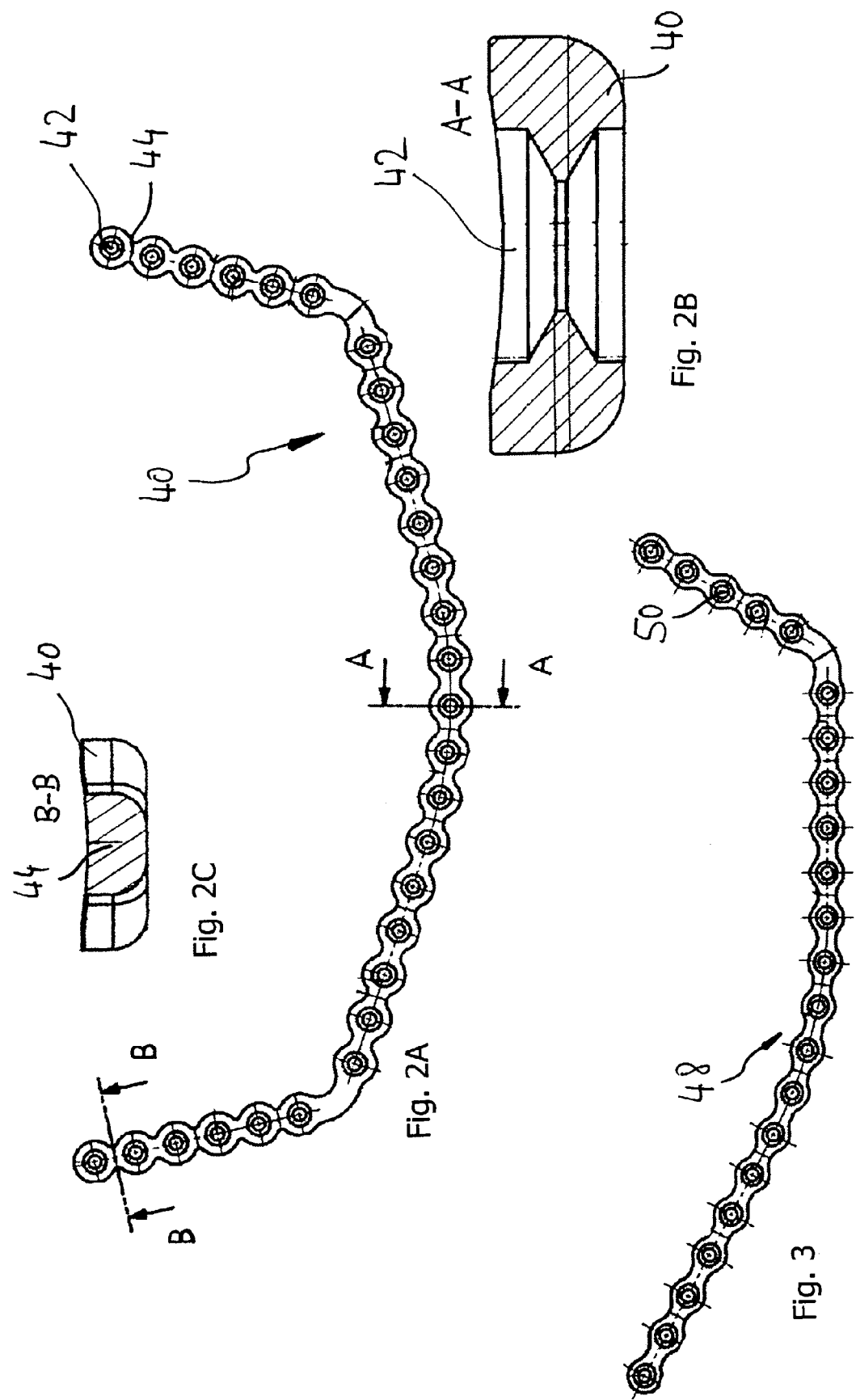

SYSTEM AND METHOD FOR PROVIDING FASTENING ELEMENTS FOR A BONE PLATE

FIELD OF THE INVENTION

The invention relates to bone plates and the fastening thereof within the framework of a surgical intervention. The invention relates in particular to aspects in connection with the provision of fastening elements, which are introduced into openings of the bone plate in order to fasten the bone plate.

BACKGROUND OF THE INVENTION

In various surgical interventions bone plates are initially fastened provisionally to a bone or bone fragment, then detached and in a further step finally fixed to the bone or bone fragment. Such a technique is used e.g. in the field of oral surgery when a removed bone segment has to be bridged by the bone plate.

Before removal of the bone segment the bone plate is generally fastened provisionally to the bone by means of suitable fastening elements such as bone screws. The purpose of this provisional fastening is to determine subsequent, final positions of the fastening elements and to mark them on the bone.

After provisional fastening of the bone plate, the latter is detached and then the bone segment is removed. The bone plate is then repositioned in a position in which it bridges the removed bone segment, and is fastened to the bone. Fastening of the bone plate is effected by disposing fastening elements at the positions of the bone, which were determined during provisional fastening of the bone plate. It is thereby ensured that the remaining bones adopt exactly the same position relative to one another as they did prior to removal of the bone segment.

The underlying object of the invention is to indicate a system which facilitates the performance of surgical interventions such as e.g. the removal of a bone segment. A further object underlying the invention is to indicate an improved method of surgically removing a bone segment.

SUMMARY OF THE INVENTION

According to the present invention a system is provided for the provision of fastening elements during a surgical intervention. The system comprises at least one bone plate having a plurality of openings, which are arranged in a first pattern, as well as a receiving surface for fastening elements, which has openings arranged in a second pattern. The second pattern is at least in sections identical or similar to the first pattern.

According to a first embodiment the system comprises at least one bone plate having a plurality of openings, which are arranged in a first pattern, and fastening elements of different geometric dimensions. The fastening elements may be introduced into the openings of the bone plate in order to fasten the latter to a bone or to a bone fragment. The system further comprises a receiving surface, which is provided with a plurality of openings for temporarily receiving the fastening elements. The openings of the receiving surface are arranged in a second pattern, which is at least in sections identical or similar to the first pattern. The number of openings forming the first pattern may be identical to the number of openings forming the second pattern. It is however also possible for the first pattern to comprise more or fewer openings than the second pattern.

According to a further embodiment of the invention a system is provided, which comprises at least one bone plate, which has a plurality of openings arranged in a first pattern for receiving fastening elements, and a receiving device for the fastening elements. The receiving device has a receiving surface, which is provided with a plurality of openings for temporarily receiving the fastening elements. The openings of the receiving surface are arranged in a second pattern, which is at least in sections identical or similar to the first pattern. The fastening elements may have different geometric dimensions, such as different lengths, different diameters, etc. The fastening elements may moreover differ in further aspects. For example, fastening elements in the form of bone screws may differ e.g. in the shape of the screw head or in the thread lead.

According to a further aspect of the invention a method of surgically removing a bone segment is provided. The method comprises holding in readiness a system for the provision of fastening elements, including a bone plate and a receiving surface, provisional positioning of the bone plate on a bone by means of a plurality of fastening elements in a position in which the bone plate bridges the bone segment to be removed, and subsequently removing the fastening elements to enable detachment of the bone plate from the bone. Each fastening element removed from a specific opening of the bone plate is in said secnario disposed in an, in each case, positionally associated opening of the receiving surface. Then the bone plate is detached and the bone segment is removed. The bone plate is then finally positioned by means of the fastening elements received by the receiving surface. In said case, each fastening element removed from a specific opening of the receiving surface is introduced into an, in each case, positionally associated opening of the bone plate. The fastening elements may be fastened to the points of the bone where they were previously disposed during provisional fastening of the bone plate. The method is suitable e.g. for removing a bone segment from a jawbone.

BRIEF DESCRIPTION OF THE DRAWINGS

Further advantages of the invention are described below with reference to the drawings and preferred embodiments. The drawings show:

FIG. 1A a perspective view of a freely positionable receiving device of the provision system according to the invention;

FIG. 1B a plan view of the receiving device according to FIG. 1A;

FIG. 1C a front view of the receiving device according to FIG. 1A;

FIG. 1D a side view of the receiving device according to FIG. 1A;

FIG. 2A a plan view of a curved bone plate of the provision system according to the invention;

FIG. 2B the bone plate according to FIG. 2A in a sectional view along the line A-A;

FIG. 2C the bone plate according to FIG. 2A in a sectional view along the line B-B;

FIG. 3 a plan view of a further bone plate of the provision system according to the invention;

DETAILED DESCRIPTION OF PREFERRED EMBODIMENTS

Figure 4A:
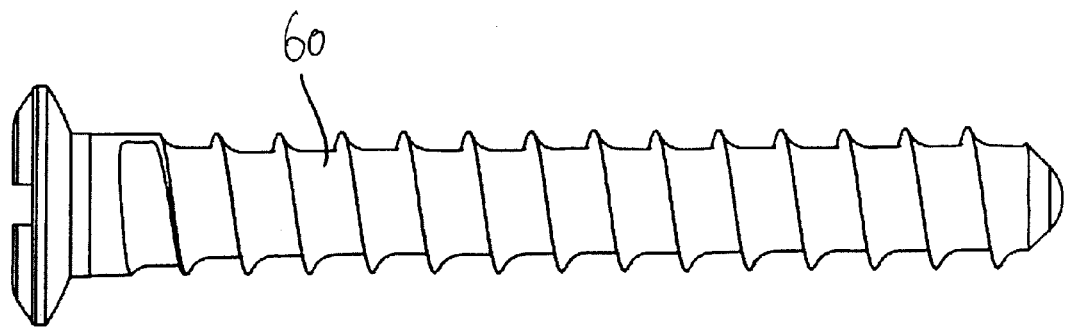
FIGS. 4A-4C fastening elements of the provision system according to the invention having different geometric dimensions.

The following description of preferred embodiments relating to a system for the provision of fastening elements and to a method of surgically removing a bone segment is merely by way of example and does not limit the scope of the invention, its application or its use. Although the provision system is described below in connection with a surgical intervention in the region of the lower jaw, the provision system is also usable for a number of further surgical interventions.

In FIGS. 1A-1D a receiving device 10 of the provision system designed in the style of a table is illustrated. The receiving device 10 comprises a rectangular, plate-shaped and substantially planar receiving surface 12 as well as support elements 14, 16, 18 extending down at right angles from the receiving surface 12. The two, in FIG. 1A front, support elements 14 and 16 have a narrow, elongate shape and the back support element 18 is of a plate-shaped design.

Formed in the receiving surface 12 is a plurality of circular through-openings 20. The openings 20 are arranged in an, in sections, curved, substantially semicircular pattern.

As FIG. 1B reveals, the openings 20 arranged in a row are provided in sections with consecutive numbering. More precisely, the openings 20 in a central arc-shaped section are numbered consecutively from 1 to 17 and in two outer linear sections 24, 26 adjoining the curved section 22 are numbered in each case from 1 to 6.

In an, in FIG. 1A, rear portion of the receiving surface 12 the receiving device 10 is provided with two elongate recesses 28, 30 extending parallel to one another for receiving screwdriver shanks. A removal opening 32 in the back, plate-shaped support element 18 facilitates removal of the shanks from the recesses 28, 30.

In FIG. 2A a first bone plate 40 of the provision system is illustrated. Said bone plate 40 is provided with a plurality of openings 42. The number of openings 42 is identical to the number of openings 20 forming a semicircular pattern in the receiving surface 12 shown in FIG. 1A. It is moreover apparent that the pattern formed by the openings 42 of the bone plate 40 is identical to the pattern formed by the openings 20 provided in the receiving surface 12 of the receiving device 10.

FIG. 2B shows the cross section of the bone plate 40 in the region of a through-opening 42. FIG. 2C shows the cross section of the bone plate 40 in the region of a web 44 connecting two openings 42.

FIG. 3 shows a further bone plate 48 of the provision system. The bone plate 48 has a plurality of openings 50, which are arranged in a pattern similar to the pattern of the openings 20 of the receiving device 12 according to FIG. 1A. In sections the pattern of the openings 50 is even identical to the pattern of the openings 20 formed in the receiving surface 12. More precisely, both patterns are identical in the region of the curved section 22 shown in FIG. 1B and in the linear region 26. The number of openings 50 of the bone plate 48 is however different from the number of openings 20 formed in the receiving surface 12.

The provision system therefore comprises two different bone plates 40, 48 having openings 42, 50 arranged in each case in a different pattern. Whereas the pattern of the openings 42 of the bone plate 40 is absolutely identical to the pattern of the openings 20 in the receiving surface 12, the pattern of the openings 50 of the bone plate 48 is only in sections identical to the pattern of the openings 20 of the receiving surface 12.

Figure 4B:
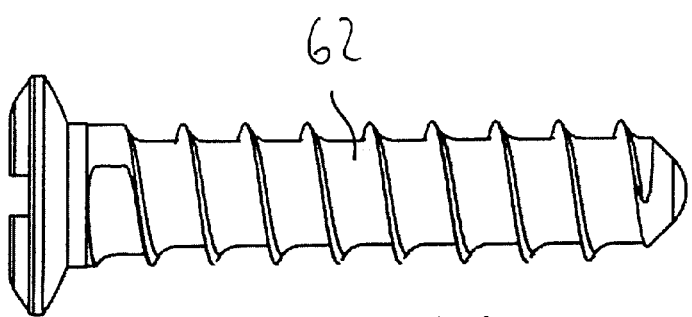
Figure 4E:
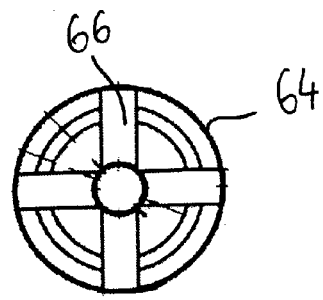
FIG. 4E a plan view of an individual one of the fastening elements according to FIGS. 4A-4C.
Figure 4C:
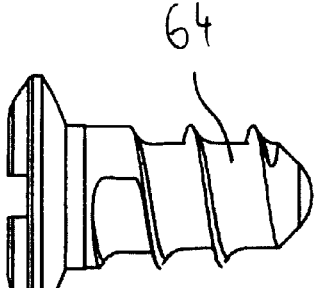

In FIGS. 4A-4C three fastening elements 60, 62, 64 of the provision system, which are of different geometric dimensions, are illustrated in side view. Said fastening elements 60, 62, 64 are bone screws for fastening the bone plates 40, 48 illustrated in FIGS. 2A and 3 to a bone or bone fragment. The individual bone screws 60, 62, 64 differ from one another in each case in their length.

Figure 4D:
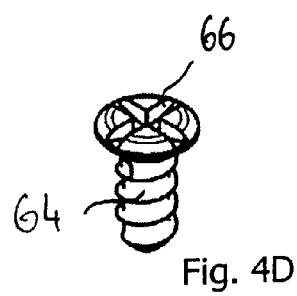
FIG. 4D a perspective view of the fastening element according to FIG. 4C.

FIG. 4D shows a perspective view of the shortest bone screw 64 and FIG. 4E a plan view of said bone screw 64. Clearly visible in each case is a cross recess structure 66, which is formed in the region of the screw head and allows a torque to be transmitted to the bone screw 64 by means of a suitable tool. The other two bone screws 60, 62 of the provision system are provided with a similar cross recess structure.

There now follows a description, with reference to the previously described components of the provision system, of the use of the provision system during surgical removal of a segment of the lower jawbone. In a first step the bone plate 40 is bent and hence adapted to the shape of the lower jawbone. Then the bone plate 40 is fastened by means of a plurality of the fastening elements illustrated in FIGS. 4A-4C provisionally in a position, in which it bridges the bone segment of the jawbone that is to be removed. For said purpose, bone screws 60, 62, 64 of differing length are used.

In a next step the provisionally fastened bone plate 40 is detached. For said purpose, the individual bone screws 60, 62, 64 are removed from the individual openings 42 of the bone plate 40 and deposited in corresponding openings 20 of the receiving surface 12 of the receiving device 10. If, for example, a bone screw is removed from the opening 42 at the top left in FIG. 2A, then said bone screw is introduced into the opening 20 provided with the number 6 of the section 24 of the receiving device 10, and so on.

After detachment of the bone plate 40, the bone segment to be removed from the lower jaw is sawn away and the bone plate 40 is then finally positioned. For said purpose, the bone plate 40 is positioned in such a way that the previous drill holes, which were formed in the bone by the individual bone screws during provisional fastening of the bone plate 40, are disposed in the region of the, in each case, associated opening 42. The bone screws 60, 62, 64 provided by the receiving device 10 are then individually picked up and re-inserted into the jawbone in order to fasten the bone plate 40. In the present case, the procedure is such that e.g. the bone screw, which is removed from the opening 20 provided with the number 6 of the section 24 of the receiving device 10, is introduced into the opening 42 of the bone plate 40 that is shown at the top left in FIG. 2A. A similar procedure is followed for the remaining bone screws provided by the receiving device 10.

Said way of proceeding has the advantage that a bone screw of a specific length may again be positioned at the correct point of the lower jawbone. The provision system therefore prevents bone screws of different length from becoming mixed up during the final fastening of the bone plate 40. If too short a screw were to be picked up by mistake, this might lead to defective fastening of the bone plate 40 and, if too long a screw were to be picked up by mistake, this might lead to damage of the jawbone.

The previously described provision system comprises bone screws 60, 62, 64 of different geometric dimensions.

The provision system might however alternatively comprise exclusively identical fastening elements.

The previous description relates to exemplary forms of construction of the present invention. The person skilled in the art is aware that different changes, modifications and variations of said forms of construction are possible without departing from the spirit and scope of the invention.

The invention claimed is:

1. A system for managing and using fastening elements during a surgical procedure, comprising:
    At least one bone plate having a plurality of openings arranged in a first pattern;
    A plurality of fastening elements having different geometric dimensions for inserting into the opening of the bone plate to fasten the bone plate to a bone or to a bone fragment; and
    a receiving device having a receiving surface with a plurality of openings arranged in a second pattern for temporarily receiving the fastening elements, wherein the first and second patterns have at least sections thereof similar to one another such that the plurality of fastening elements can be temporarily stored in the receiving device in positions associated with their positions in the bone plate, wherein the receiving device is defined as a table including at least one leg member.

2. The system according to claim 1, wherein the number of openings forming the first pattern is lower than or identical to the number of openings forming the second pattern.

3. The system according to claim 1, wherein the openings of the receiving surface are provided with, at least in sections, consecutive numbering indicated on the receiving device.

4. The system according to claim 1, wherein the receiving device is portable.

5. The system according to claim 1, wherein the fastening elements are further defined as bone screws.

6. A system for managing and using fastening elements during a surgical procedure, comprising:
    At least one bone plate having a plurality of openings arranged in a first pattern for receiving fastening elements; and
    a receiving device having a receiving surface,
    wherein the receiving surface is provided with a plurality of openings for temporarily receiving the fastening elements and wherein the openings of the receiving surface are arranged in a second pattern, which is identical to the first pattern such that the fastening elements can be temporarily stored in the receiving device in positions associated with their positions in the bone plate, wherein the receiving device is defined as a table including at least one leg member.

7. The system according to claim 6, further comprising a plurality of fastening elements of different dimensions.

8. The system according to claim 7, wherein the fastening elements are of different lengths.

9. The system according to claim 7, wherein the fastening elements are bone screws.

10. The system according to claim 6, wherein the first pattern and the second pattern have, at least in sections, a curved shape.

11. The system according to claim 6, wherein the number of openings forming the first pattern is lower than or identical to the number of openings forming the second pattern.

12. The system according to claim 6, wherein the openings disposed in the receiving surface are, at least in sections, provided with consecutive numbering indicated on the receiving device.

13. The system according to claim 6, comprising two or more bone plates, the respective openings of which are arranged in different first patterns.

14. The system according to claim 13, wherein the openings in the receiving surface are arranged in correspondingly different second patterns.

15. The system according to claim 13, wherein the second pattern of the openings in the receiving surface is in sections identical to each of the different second patterns.

16. The system according to claim 6, wherein the openings forming the first and second patterns are disposed in a row.

17. The system according to claim 6, wherein the receiving device has a recess for receiving a screwdriver shank.

18. A method of surgically removing a bone segment, comprising:
    providing a bone plate having a plurality of openings arranged in a first pattern for receiving fastening elements;
    providing a receiving surface with a plurality of openings arranged in a second pattern similar to the first pattern at least in sections for temporarily receiving the fastening elements;
    provisionally positioning the bone plate with a plurality of fastening elements in a position in which the bone plate bridges the bone segment to be removed;
    removing the plurality of fastening elements from the bone plate to enable detachment of the bone plate, wherein each fastening element removed from a specific opening of the bone plate is disposed in a positionally associated opening of the receiving surface;
    detaching the bone plate and removing the bone segment; and
    positioning the bone plate with the fastening elements received by the receiving surface, wherein each fastening element removed from a specific opening of the receiving surface is introduced into the positionally associated opening of the bone plate.

19. The method according to claim 18, wherein the bone segment is removed from a jawbone.

20. A system for managing and using fastening elements during a surgical procedure, comprising:
    two or more bone plates having a plurality of openings arranged in different first patterns for receiving fastening elements; and
    a receiving device having a receiving surface; wherein the receiving surface is provided with a plurality of openings for temporarily receiving the fastening elements and wherein the openings of the receiving surface are arranged in a second pattern, which is identical to at least one of the first patterns such that the fastening elements can be temporarily stored in the receiving device in positions associated with their positions in the bone plate, wherein the receiving device is defined as a table including at least one leg member.

21. The system according to claim 20, wherein at least one of the first patterns and the second pattern have, at least in sections, a curved shape.

22. The system according to claim 20, wherein the number of openings forming at least one of the first patterns is lower than or identical to the number of openings forming the second pattern.

23. The system according to claim 20, wherein the openings disposed in the receiving surface are, at least in sections, provided with consecutive numbering indicated on the receiving device.

24. The system according to claim 20, wherein the openings in the receiving surface are arranged in correspondingly different second patterns.

25. The system according to claim 24, wherein the second pattern of the openings in the receiving surface is in sections identical to each of the different second patterns.

26. The system according to claim 20, wherein the openings forming the first and second patterns are disposed in a row.

27. A system for managing and using fastening elements during a surgical procedure, comprising:

At least one bone plate having a plurality of openings arranged in a first pattern for receiving fastening elements; and a receiving device having a receiving surface, wherein the receiving surface is provided with a plurality of openings for temporarily receiving the fastening elements and wherein the openings of the receiving surface are arranged in a second pattern, which is identical to the first pattern such that the fastening elements can be temporarily stored in the receiving device in positions associated with their positions in the bone plate, wherein the receiving device is defined as a table including at least one leg member;

wherein the receiving device has a recess for receiving a screwdriver shank.

* * * * *